US008512225B2

(12) United States Patent
Lee

(10) Patent No.: US 8,512,225 B2
(45) Date of Patent: Aug. 20, 2013

(54) PLATED GLASS DILDO

(75) Inventor: Calvin Spencer Lee, Northridge, CA (US)

(73) Assignee: Wing Pow International Corp., Chatsworth, CA (US)

( * ) Notice: Subject to any disclaimer, the term of this patent is extended or adjusted under 35 U.S.C. 154(b) by 1004 days.

(21) Appl. No.: 12/506,979

(22) Filed: Jul. 21, 2009

(65) Prior Publication Data

US 2011/0021870 A1 Jan. 27, 2011

(51) Int. Cl.
*A61F 5/00* (2006.01)

(52) U.S. Cl.
USPC .......... 600/38; 601/46

(58) Field of Classification Search
USPC .......... 600/38–41; 601/46
See application file for complete search history.

(56) References Cited

U.S. PATENT DOCUMENTS

| | | | | |
|---|---|---|---|---|
| 3,749,089 | A | 7/1973 | Derr | |
| 5,853,362 | A | 12/1998 | Jacobs | |
| 6,132,366 | A | 10/2000 | Ritchie et al. | |
| 6,533,718 | B1 | 3/2003 | Ritchie et al. | |
| 6,723,031 | B1 * | 4/2004 | Wild | 600/38 |
| 7,946,977 | B2 * | 5/2011 | Klearman et al. | 600/38 |
| 2003/0097041 | A1 | 5/2003 | Ritchie et al. | |
| 2003/0149337 | A1 | 8/2003 | Ritchie et al. | |
| 2004/0193080 | A1 | 9/2004 | Siddhartha | |
| 2005/0039683 | A1 | 2/2005 | Kanai et al. | |
| 2008/0039683 | A1 | 2/2008 | Clupper | |
| 2008/0188709 | A1 | 8/2008 | Gil | |
| 2009/0234182 | A1 | 9/2009 | Buchholz | |

FOREIGN PATENT DOCUMENTS

| | | | |
|---|---|---|---|
| DE | 9011708 | U1 | 10/1990 |
| DE | 20119660 | U1 | 6/2002 |
| DE | 202006002812 | U1 | 9/2006 |
| WO | 2008077144 | A1 | 6/2008 |

OTHER PUBLICATIONS

Chen, Jason; Gold Plated Vibrator; Aug. 6, 2007.*
European Search Report, Issued on Sep. 21, 2010 in European Patent Application No. 10007091.
The Original Glass Dildo—www.originalglassdildo.com. p. 5 discloses a color coated glass dildo—Date 1998.

* cited by examiner

*Primary Examiner* — Jack Lacyk
(74) *Attorney, Agent, or Firm* — Jeffrey G. Sheldon; Sheldon Mak & Anderson

(57) ABSTRACT

A dildo, including a solid high density heat-resistant glass substrate completely covered by a relatively inert metal plating such as gold, silver, nickel, chromium or titanium, the substrate having a shaft portion, a base portion at one end and a head portion at the opposite end. In one configuration the head and base portions are enlarged, the shaft portion having spaced protuberances. In another configuration the shaft portion is serpentine in form, the head portion is tapered and having a hole formed there through for a tether, and the base portion has oppositely projecting protuberances. The metal plating can have a variety of coloring patterns.

9 Claims, 2 Drawing Sheets

PLATED GLASS DILDO

BACKGROUND

The present invention relates to sexual stimulation devices, and more particularly to a glass dildo.

Sexual stimulation devices of the prior art include dildos that have vibratory elements such as disclosed in U.S. Application Publication No 2002/1013415 and International Publication No. WO 2007/041853. It is also known to provide arcuate deformation of a prosthetic device such as a dildo as disclosed in U.S. Application Publication No. 2006/0069329. Another class of dildos avoids vibratory and other powered forms of stimulation, relying primarily on the shape of a rigid or semi-rigid device, such as disclosed in U.S. Pat. No. 5,853,362 to Jacobs and U.S. Pat. No. 6,533,718 to Ritchie et al. Materials disclosed as suitable for these devices include wood, metal, plastic, rubber, wax, glass and composite material. It is also known to use Pyrex glass for such devices. However, it is believed that none of this class of devices of the prior art has proven entirely satisfactory, for a variety of reasons. For example, known colored coatings for Pyrex glass are believed to be toxic, requiring an outer layer of Pyrex glass to be added, significantly increasing the cost. Also, the use of solid metal has the disadvantage of inferior heat retention as compared with Pyrex.

Thus there is a need for a sexual stimulation device in the form of a dildo that provides improved appearance and heat retention as compared with existing devices.

SUMMARY

The present invention meets this need by providing a dildo that looks like solid metal yet has exceptional heat retention. In one aspect of the invention, the dildo includes a solid glass substrate substantially in the form of an erect penis, and a plated metal coating. The substrate can include a generally cylindrical shaft portion, an enlarged head portion at a first end of the substrate, and a base portion at an opposite second end of the substrate. The substrate can further include a plurality of spaced apart raised protuberances between the head portion and the base portion. The raised protuberances can include a spaced array of rounded circular projections, and can further include a generally helical rounded ridge formation.

The base portion can include a generally spherical enlargement, and can further include a generally ellipsoidal enlargement connecting the spherical enlargement to the shaft portion.

In another aspect of the invention, the substrate can include a generally serpentine shaft portion, an enlarged base portion at a first end of the shaft portion, and a tapered head portion at an opposite second end of the shaft portion. The base portion can have a pair of protuberances projecting from opposite sides thereof. The head portion can have an opening formed there through for attaching a tether.

Preferably the metal coating completely covers the substrate for conveying the appearance of a solid metal dildo. The metal coating can include titanium and/or chromium.

DRAWINGS

These and other features, aspects, and advantages of the present invention will become better understood with reference to the following description, appended claims, and accompanying drawings, where:

DESCRIPTION

Figure 1:
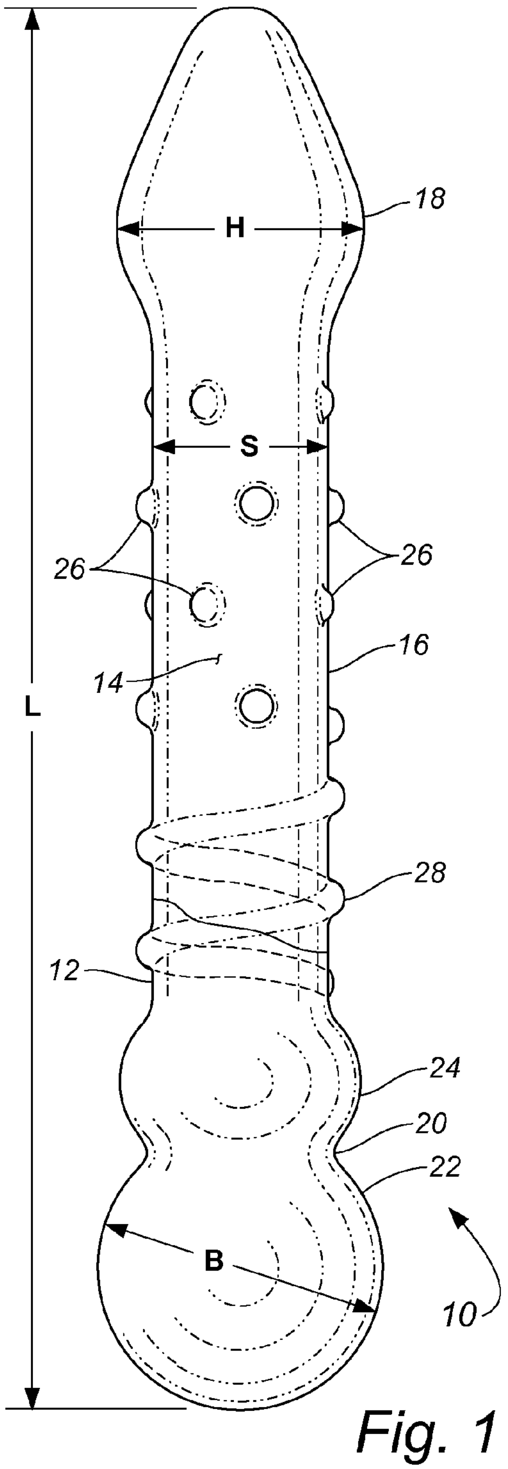
FIG. 1 is a front view of a plated glass dildo according to the present invention.
Figure 2:
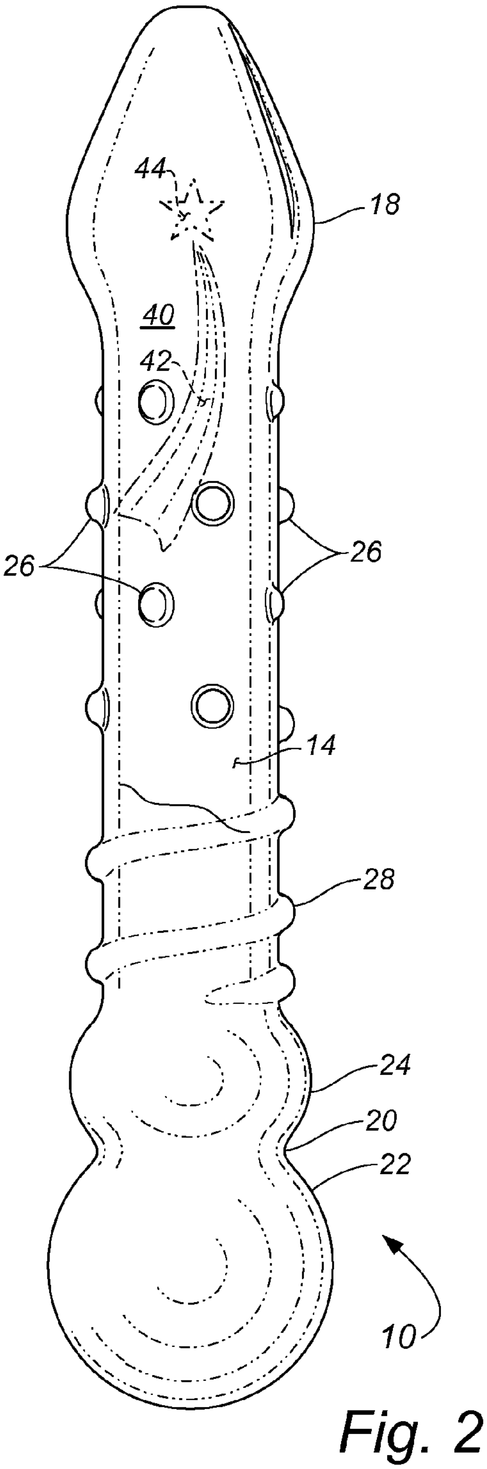
FIG. 2 is a lateral view of the dildo of FIG. 1.

The present invention is directed to a plated glass dildo that is particularly effective in retaining stored heat yet having the appearance of metal. With reference to FIGS. 1 and 2 of the drawings, a plated glass dildo 10 includes a solid, high density heat-resistant glass substrate 12 substantially in the form of an erect penis, and a plated metal coating 14, the coating preferably covering the entire surface of the substrate. The substrate 12 includes a generally cylindrical shaft portion 16, an enlarged head portion 18, and a base portion 20. As used herein "generally" means approximately, and "generally cylindrical" means of approximately uniform rounded cross-section. In the exemplary embodiment of FIGS. 1 and 2, the base portion includes a generally spherical main handle portion 22 and an ellipsoidal secondary handle portion 24. The shaft portion 16 also has a plurality of protuberances, including a spaced array of rounded knobs 26 and a somewhat helically shaped rounded ridge 28, the ridge being spaced between the array of knobs 26 and the base portion 20.

Particularly suitable high density heat-resistant glass for the substrate 12, known as Pyrex glass, is commercially available from a variety of sources. A typical overall length L is 8 inches, with a handle portion diameter B of 1.5 inches, a head diameter H of 1.25 inches, and a shaft diameter S of 1.0 inches. Suitable relatively inert metals for the plated coating can include gold, silver, nickel, chromium and titanium. Plating can be by electroplating, following application of a thin electroless coating of a conductive material such as copper as is known in plating practice. Electroless plating involves deposition of a metal coating by immersion of a metal or nonmetal in a suitable bath. Alternatively, the plating can be by vacuum metalizing as is well known by those skilled in the plating art. Preferably the plating is polished for improved appearance and ease of cleaning.

The plating can be in different colors. For example, chrome and titanium plating can be provided in a variety of colors, such as gold, silver, red, blue, and green. Further, the plating can be colored in a variety of surface patterns such as rainbow effects, and localized zones having different colorations. In the exemplary configuration of the dildo 10 shown in FIGS. 1 and 2, the metal coating 14 includes a first colored region 40 of a solid color such a beige, a second colored region 42 having a rainbow pattern, and a third colored region 44 of a single solid color such as red as shown in FIG. 2.

Figure 3:
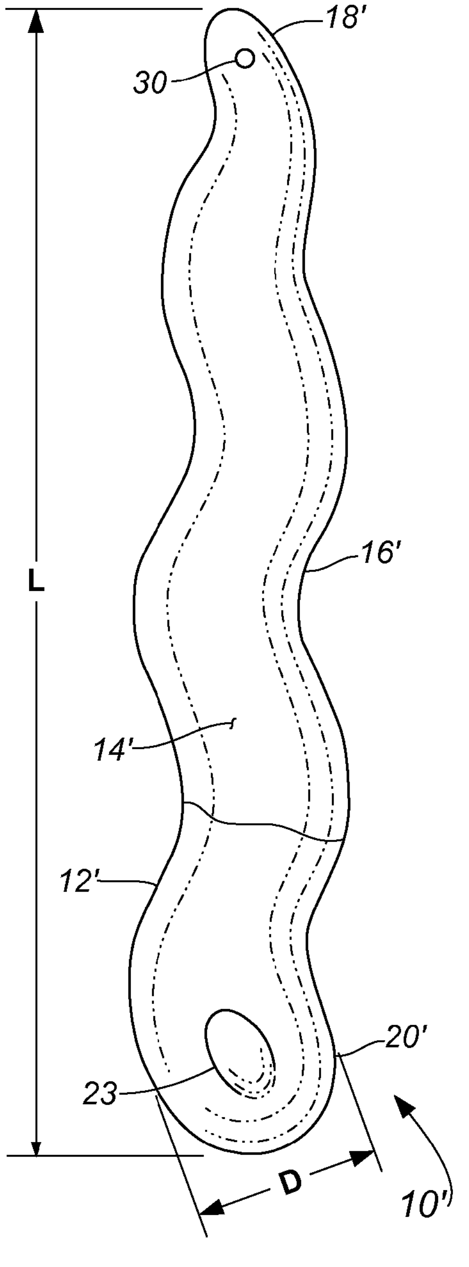
FIG. 3 is a front view showing an alternative configuration of the dildo of FIG. 1.
Figure 4:
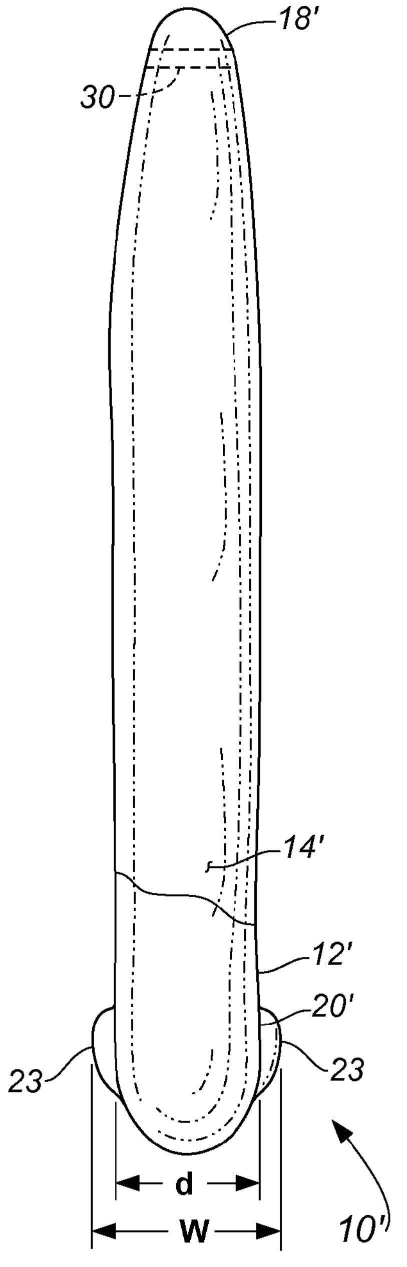
FIG. 4 is a lateral view of the dildo of FIG. 3.

With further reference to FIGS. 3 and 4, an alternative configuration of the plated glass dildo, designated 10', includes counterparts of the substrate, designated 12', and the plated metal coating, designated 14'. The substrate 12' includes a generally serpentine shaft portion 16', an tapered head portion 18', and a rounded base portion 20' having oppositely projecting protuberances 23. Also, a laterally oriented opening 40 extends through the head portion 18' for attaching a tether (not shown). The base portion 20' including the protuberances 23 can serve as a handle; alternatively, the head portion 18' together with the tether (when attached) can serve as a handle.

In the configuration of FIGS. 3 and 4, exemplary dimensions of the substrate 12' include an overall length L of 6 inches, the base portion 20' being generally elliptical in cross-section and having a major diameter D of 0.9 inches and a minor diameter d of 0.75 inches, the protuberances' 23 projecting to an overall width W of 1.0 inch overall. Preferably, in the configurations of FIGS. 1 and 2 as well as FIGS. 3 and 4, the overall length L is between approximately 3 inches and 12 inches.

Although the present invention has been described in considerable detail with reference to certain preferred versions thereof, other versions are possible. For example, the shaft portion in the configuration of FIGS. 1 and 2 can be curved or serpentine. Also, the shaft portion in the configuration of FIGS. 3 and 4 can be provided with counterparts of the protuberances of the configuration of FIGS. 1 and 2. Further, the head portion 18' in the configuration of FIGS. 3 and 4 can be enlarged. Therefore, the spirit and scope of the appended claims should not necessarily be limited to the description of the preferred versions contained herein.

What is claimed is:

1. A dildo comprising:

(a) an elongate solid heat-resistant glass substrate adapted to retain heat, the dildo as a whole being adapted to remain heated during operation, wherein the substrate is substantially in the form of an erect penis, the substrate comprising:
   (i) a generally cylindrical shaft portion;
   (ii) an enlarged head portion at a first end of the substrate;
   (iii) a base portion comprising a generally spherical enlargement at an opposite second end of the substrate; and
   (iv) a generally ellipsoidal enlargement connecting the spherical enlargement to the shaft portion; and (b) a plated metal coating completely covering the substrate.

2. The dildo of claim 1, wherein the substrate further comprises a plurality of spaced apart raised protuberances between the head portion and the base portion.

3. The dildo of claim 2, wherein the raised protuberances comprise a spaced array of rounded circular projections.

4. The dildo of claim 2, wherein the protuberances include a generally helical rounded ridge formation.

5. The dildo of claim 1, wherein the metal coating comprises chromium.

6. The dildo of claim 5, wherein at least a portion of the metal coating is colored with an additional coloring material.

7. The dildo of claim 6, wherein the coloring material is in a predetermined pattern of different colors.

8. The dildo of claim 1, wherein the substrate has an overall length of between approximately 3.0 inches and 12.0 inches.

9. A dildo comprising:

(a) a solid glass substrate substantially in the form of an erect penis, comprising:
   (i) a generally cylindrical shaft portion having a plurality of spaced apart raised protuberances;
   (ii) an enlarged head portion at a first end of the substrate,
   (iii) a base portion comprising a generally spherical enlargement at an opposite second end of the substrate; and
   (iv) a generally ellipsoidal enlargement connecting the spherical enlargement to the shaft portion; and (b) a plated metal coating completely covering the substrate and comprising chromium.

* * * * *